United States Patent [19]
Lieber et al.

[11] 3,981,197
[45] Sept. 21, 1976

[54] EXTERNAL BLOOD PRESSURE TRANSDUCER

[75] Inventors: Clement Eugene Lieber, Yorba Linda; Lawrence Webster Blake, Costa Mesa, both of Calif.

[73] Assignee: American Hospital Supply Corporation, Evanston, Ill.

[22] Filed: June 23, 1975

[21] Appl. No.: 589,714

[52] U.S. Cl. .............................. 73/398 AR; 338/4; 338/42
[51] Int. Cl.² .................................... G01L 9/06
[58] Field of Search ............. 73/398 AR; 338/4, 36, 338/42, 255

[56] References Cited
UNITED STATES PATENTS 3,315,201  4/1967  Werme .................. 338/42 X
3,473,386  10/1969  Nielsen et al. ............... 73/398 AR

FOREIGN PATENTS OR APPLICATIONS 1,447,317  6/1966  France ..................... 73/398 AR
2,130,390  12/1972  Germany ................... 73/398 AR

*Primary Examiner*—James J. Gill
*Attorney, Agent, or Firm*—Lee R. Schermerhorn

[57] ABSTRACT

Piezoresistive deflection-sensitive beam elements are encapsulated in a disc of elastomeric material which forms a fluid pressure responsive diaphragm. The beam elements are oriented within the diaphragm so as to be strained in tension or compression when the diaphragm is deformed by fluid pressure. The beam elements are connected in a bridge circuit to produce an electric signal which provides a fluid pressure indication or measurement, as in a blood pressure monitoring catheter.

11 Claims, 5 Drawing Figures

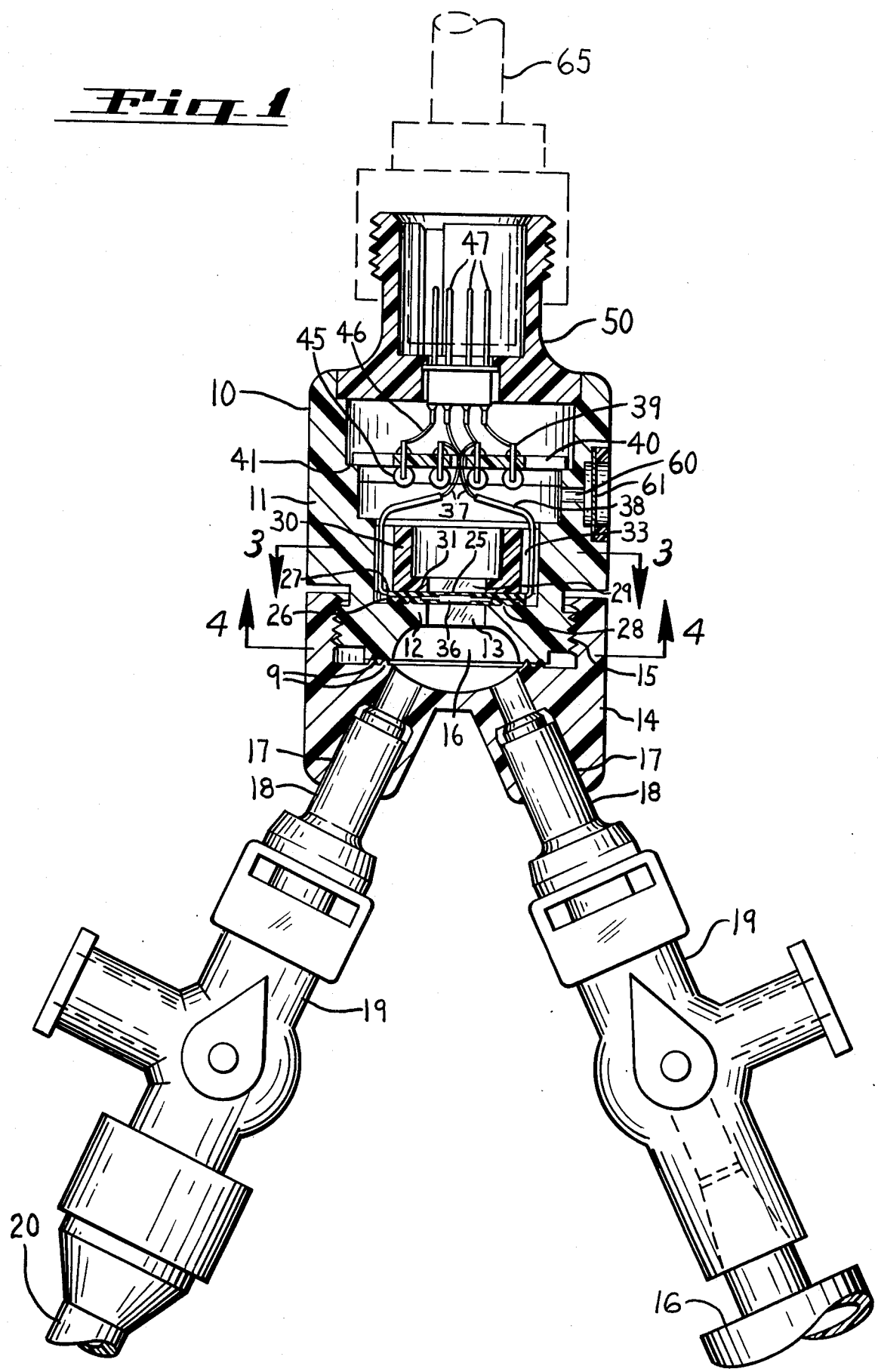

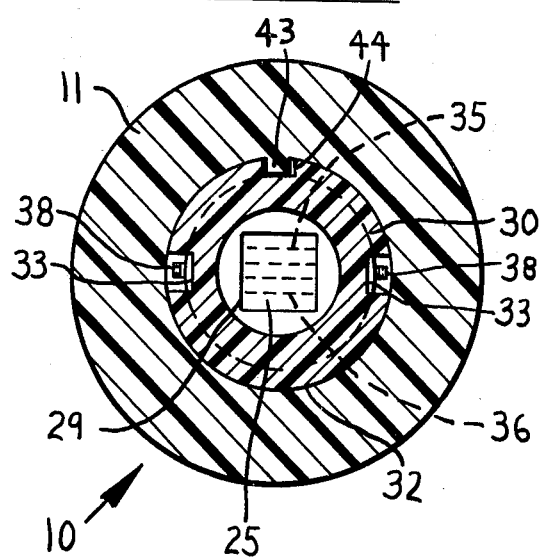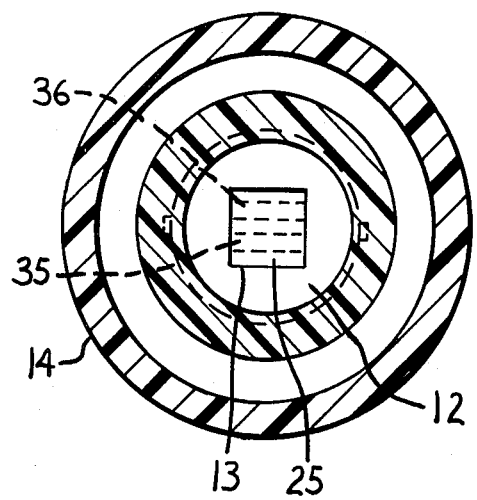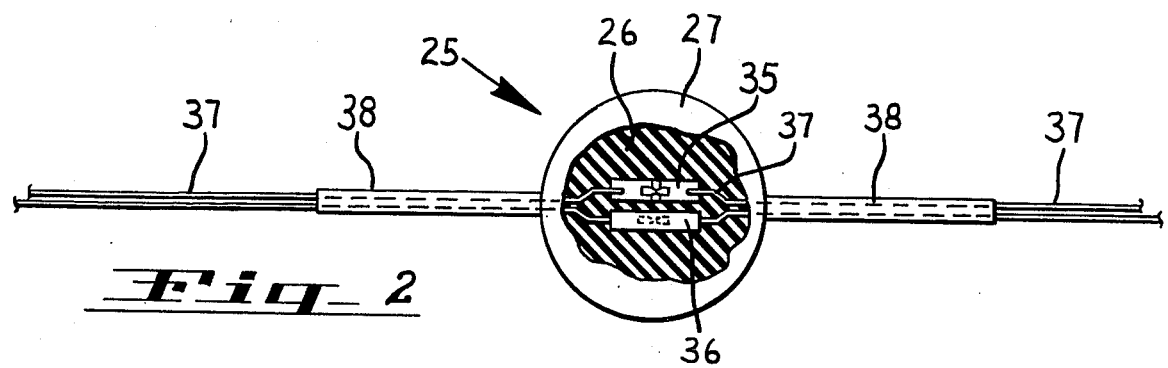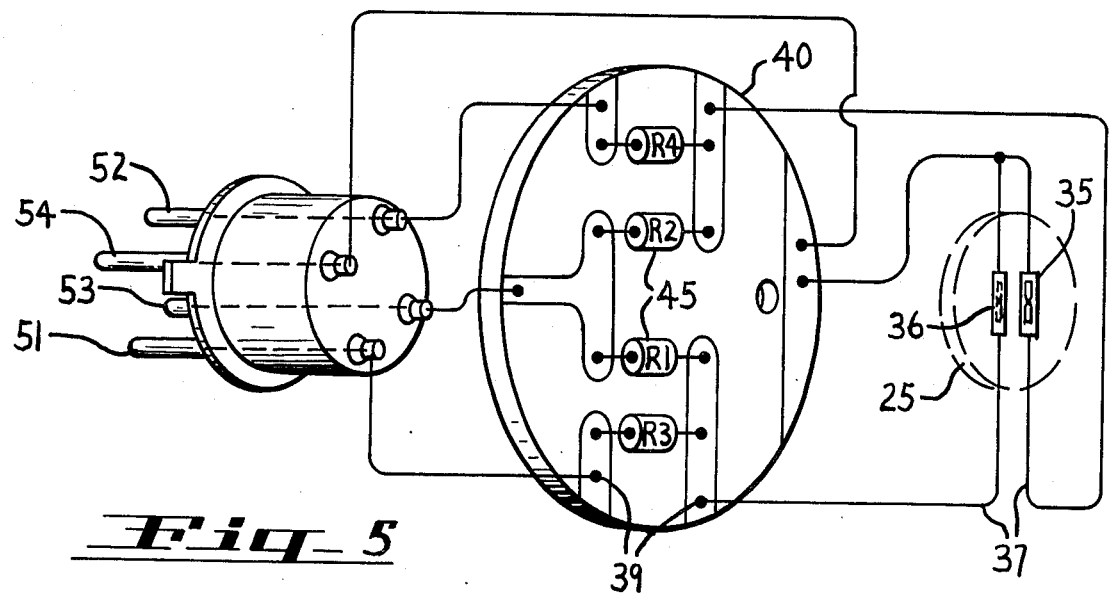

EXTERNAL BLOOD PRESSURE TRANSDUCER

BACKGROUND OF THE INVENTION

This invention relates to a fluid pressure transducer and has particular reference to an extracorporeal blood pressure monitoring device.

Devices heretofore proposed for this purpose have been deficient in sensitivity and patient safety, of relatively fragile construction and have been complicated and expensive to manufacture.

Objects of the present invention are, therefor, to provide an improved fluid pressure transducer, to provide an improved extracorporeal blood pressure transducer and to provide a device of the type described which has greater sensitivity, which embodies good electrical isolation for patient safety, good mechanical shock resistance and which is less costly to manufacture.

SUMMARY OF THE INVENTION

In the present construction, one or more piezoresistive deflection-sensitive beam elements are encapsulated in a disc of elastometric material which forms a fluid pressure responsive diaphragm. The beam elements are oriented within the diaphragm so as to be strained in tension or compression when the diaphragm is deformed by fluid pressure. The beam elements are connected in a half or full bridge circuit to produce an electric signal which provides a fluid pressure indication or measurement when used, for example, in connection with a suitable read-out device and a blood pressure monitoring catheter.

The invention will be better understood and additional objects and advantages will become apparent from the following description of the preferred embodiment illustrated in the accompanying drawings. Various changes may be made, however, in the details of construction and arrangement of parts and certain features may be used without others. All such modifications within the scope of the appended claims are included in the invention.

BRIEF DESCRIPTION OF THE DRAWINGS

FIG. 1 is an enlarged view with parts in section showing an external blood pressure transducer embodying the invention;

FIG. 2 is a view of the pressure responsive diaphragm with parts broken away;

FIG. 3 is a view on the line 3—3 in FIG. 1;

FIG. 4 is a view on the line 4—4 in FIG. 1; and

FIG. 5 is an exploded view showing the circuit connections.

DESCRIPTION OF THE PREFERRED EMBODIMENT

The present transducer and its associated circuit elements are mounted in a housing 10 having a cylindrical side wall 11 and a bottom wall 12 surrounding a square central opening 13 as shown in FIG. 1. A dome member 14 has screw-threaded engagement at 15 with bottom wall 12. Confronting cavities in dome 14 and bottom wall 12 form a fluid pressure chamber 16 in communication with opening 13. A raised circular lip or ridge 9 assures an effective seal between housing 10 and dome member 14.

Dome 14 is molded in one piece with a pair of convergent bores 17 to receive conventional connector fittings 18. In the present illustration, by way of example, these connector fittings in turn receive a pair of valves 19. One of the valves 19 is connected to a tube 20 such as a catheter tube communicating with some part of the vascular system of a patient whose blood pressure is to be monitored. The other valve 19 is adapted to be connected to other equipment or apparatus, as for example for flushing and washing the chamber 16.

Opening 13 is sealed by a flexible diaphragm 25 which is deflected by the fluid pressure in chamber 16. Diaphragm 25 preferably comprises a bottom disc 26 of black natural rubber and a top disc 27 of clear natural rubber. Natural rubber is preferred because of its lower dampening properties in comparison with synthetic rubbers.

Rubber discs 26 and 27 are vulcanized together and encapsulated between these discs is one or more deflection-sensitive beam elements such as the pair of beam elements 35 an 36 in FIG. 2. The beam element or elements are disposed in approximately diametral position in the diaphragm so that their end portions are clamped in fixed positions between retainer ring 30 and bottom wall 12 at opposite sides of openings 13 and 29 while the middle portions of the beam elements are free to flex with the central portion of the diaphragm. This allows both positive and negative gage pressures to be measured and minimizes hysteresis, non-linearity, sensitivity changes and null drift under pressure.

Bottom wall 12 may be provided with a plurality of concentric circular ridges 28 which become embedded in the bottom disc of the diaphragm to seal the diaphragm against bottom wall 12 and prevent any leakage of fluid through opening 13 to the inside of housing 10.

This seal is maintained by a cylindrical retainer ring 30 which has a bottom surface 31 engaging the top face of the diaphragm over the ridges 28. The periphery of retainer ring 30 is bonded to the surface of a cylindrical bore 32 which extends upward from bottom wall 12. Thus, the marginal portion of diaphragm 25 is clamped and sealed against bottom wall 12 while the central portion of the diaphragm spans the opening 13 and a similar square opening 29 in retainer ring 30 whereby the central portion of the diaphragm is free to deflect upward or downward in response to fluid pressure variations in opening 13. As shown in FIG. 3, the opening 29 is maintained in register with opening 13 by a spline 43 in bore 32 and a groove 44 in retainer ring 30.

This mounting of the diaphragm from the top of housing 10 allows dome member 14 to be screwed up tightly onto the housing without disturbing the diaphragm.

The bottom face of the diaphragm which is exposed to the pressurized liquid is coated with an elastomer such as bromo-butyl rubber that is very impervious to moisture. This prevents the diaphragm from absorbing moisture and thereby swelling and changing its physical and, consequently, electrical characteristics.

When there is a pair of beam elements as shown in FIG. 2, one of them is disposed in a position to be strained in tension, causing an electrical resistance increase, while the other beam element is disposed in a position to be strained in compression, causing an electrical resistance decrease, in response to fluid pressure in chamber 16 and opening 13.

The beam elements, typified by beam elements 35 and 36, can all be oriented in tension, compression or combinations thereof for making up the various legs of a strain gage bridge. Typically, the beam elements are encapsulated in pairs to form a half strain gage bridge, with one beam in tension and the other in compression for providing maximum sensitivity. This is done by merely turning one beam upside down with respect to the other as shown in FIG. 2.

The full bridge unit can be assembled using fixed resistances to balance and complete the bridge, and using load resistors to provide a standardized sensitivity. The unit can be assembled as a half bridge with the rest of the bridge being supplied by additional electronics. Or the full bridge can be composed of four or more beam elements encapsulated within the diaphragm and its sensitivity standardized by load resistors.

Beam elements 35 and 36 are connected with conductor wires 37 which extend out of the edge of the diaphragm on its opposite sides. Each pair of wires 37 is encapsulated in a rubber sheath 38 which is trained through an axial groove 33 in the periphery of retainer ring 30 as shown in FIG. 1.

In vulcanizing the discs 26 and 27 together to encapsulate beam elements 35 and 36, the wires 37 are disposed in radial positions in grooves provided in the vulcanizing dies. Rubber from one or both of discs 26 and 27 is extruded into these grooves to form the sheaths 38 which are thereby integral with the diaphragm 25 as shown in FIG. 2. By using clear rubber for one of the discs, preferably upper disc 27, factory inspection of the positions of beam elements 35 and 36 in the vulcanized diaphragm is facilitated.

Deflection-sensitive beam elements 35 and 36 are preferably of the types shown in the Hutchins U.S. Pat. Nos. 3,710,781; 3,844,026 and the Hutchins application Ser. No. 465,236 filed Apr. 29, 1974, now U.S. Pat. No. 3,905,005.

Wires 37 are connected to certain terminals indicated generally at 39 in a circuit board 40 which is mounted on a shoulder 41 in the upper end of housing 10 as shown in FIG. 1. Circuit board 40 also carries a plurality of resistors indicated generally at 45 in a bridge circuit with the beam elements 35 and 36. Other wires indicated generally at 46 in FIG. 1 connect certain terminals in the circuit board with contact pins indicated generally at 47 in an external electrical connector fitting 50. Fitting 50 is cemented to housing 10 and the space between circuit board 40 and fitting 50 is preferably potted with a suitable plastic material.

A preferred form of bridge circuit for the present purpose is shown by way of example in FIG. 5. Connector pins 51 and 52, which are two of the pins indicated generally at 47 in FIG. 1, are respectively negative and positive dc input terminals. Pins 53 and 54 are respectively negative and positive output terminals which are connected to a suitable readout device such as an electronic display device, an oscilloscope display or a chart recorder. The output signal varies with the deflection of diaphragm 25 and beam elements 35 and 36 in a well known manner in response to variations in fluid pressure on the diaphragm. Resistances R1 and R2 are fixed bridge resistors and R3 and R4 are load resistors, as indicated generally at 45 in FIG. 1.

It is desired to maintain atmospheric pressure on the upper side of diaphragm 25. For this purpose the side wall 11 of housing 10 is provided with an external vent opening 60 communicating with the space between the diaphragm and circuit board 40. Opening 60 is covered by a gas permeable-liquid impermeable membrane 61, such as porous Teflon, which prevents the entrance of moisture into housing 10. Alternatively, the space above diaphragm 25 may be vented to atmosphere through connector fitting 50 and a tube in electric cable 65.

The major parts 10, 14, 30, 40 and 50 are made of plastic and diaphragm 25 is made of natural rubber, thereby providing good electrical isolation for patient safety, making the transducer light in weight and providing good mechanical shock resistance. Also, the present form of construction is less costly to manufacture than conventional devices for this purpose.

What is claimed is:

1. In a fluid pressure transducer, a flexible diaphragm of elastomeric material, a strain gage beam element encapsulated in said elastomeric material, and electrical connections for said beam element encapsulated in said elastomeric material, said diaphragm comprising a pair of discs of said elastomeric material bonded together with said beam element disposed between said discs, at least one of said discs being transparent to provide inspection of the position of said beam element in the diaphragm.

2. A transducer as defined in claim 1, said elastomeric material being natural rubber.

3. A transducer as defined in claim 1, said diaphragm being coated with a highly moisture impermeable coating such as a bromo-butyl elastomer.

4. A transducer as defined in claim 1, said diaphragm comprising a pair of discs of said elastomeric material bonded together face to face, said beam element comprising a piezoresistive device disposed in approximately diametral position between said discs, and a sheath of said elastomeric material integral with at least one of said discs extending from the edge of said diaphragm and containing said electrical connections.

5. A transducer as defined in claim 4 including a sheath for said electrical connections extending radially from each of two opposite sides of the diaphragm, said sheaths comprising material extruded from at least one of said discs.

6. In a fluid pressure transducer, a diaphragm comprising a pair of discs of elastomeric material bonded together face to face, a strain gage beam element encapsulated between said discs, a housing for said diaphragm having a supporting surface engaging the peripheral portion of one face of the diaphragm, and a retainer ring engaging the peripheral portion of the opposite face of the diaphragm, the opposite ends of said beam element extending between said supporting surface and said retainer ring.

7. A transducer as defined in claim 6, said retainer ring having a cylindrical surface secured in said housing, and axial grooves in said cylindrical surface for electrical connections to said beam element.

8. A transducer as defined in claim 6 including concentric ridges on said supporting surface arranged to indent themselves in said one face of said diaphragm and seal said face to said supporting surface.

9. A transducer as defined in claim 6 including registering openings in said supporting surface and retainer ring having a pair of opposite parallel edges, and a plurality of said beam elements in side by side positions in said diaphragm spanning said openings, the opposite ends of all of said beam elements extending beyond said opposite edges of said openings and between said supporting surface and said retainer ring.

10. A transducer as defined in claim 9, said beam elements comprising piezoresistive devices arranged so that deflection of the diaphragm under said fluid pressure will strain certain of said devices in tension and other of the devices in compression.

11. A transducer as defined in claim 9, said registering openings being of rectangular configuration.

* * * * *